US011221492B2

(12) United States Patent
Fan et al.

(10) Patent No.: US 11,221,492 B2
(45) Date of Patent: Jan. 11, 2022

(54) EYE TRACKING APPARATUS AND EYE TRACKING DEVICE FOR THE ESTIMATION OF LINE-OF-SIGHT AND/OR GAZE POINT OF EYES

(71) Applicant: BEIJING 7INVENSUN TECHNOLOGY CO., LTD., Beijing (CN)

(72) Inventors: Yunchao Fan, Beijing (CN); Junsheng Li, Beijing (CN); Yunfei Wang, Beijing (CN); Tongbing Huang, Beijing (CN)

(73) Assignee: BEIJING 7INVENSUN TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 16/868,453

(22) Filed: May 6, 2020

(65) Prior Publication Data
US 2020/0379263 A1 Dec. 3, 2020

(30) Foreign Application Priority Data
Jun. 3, 2019 (CN) .......................... 201910477708.9

(51) Int. Cl.
*G02B 27/01* (2006.01)
*A61B 3/113* (2006.01)
(Continued)

(52) U.S. Cl.
CPC .......... *G02B 27/0176* (2013.01); *A61B 3/113* (2013.01); *G02B 27/0093* (2013.01);
(Continued)

(58) Field of Classification Search
CPC ............ G02B 27/0176; G02B 27/0093; G02B 27/0172; G02B 2027/0138;
(Continued)

(56) References Cited

U.S. PATENT DOCUMENTS 1,208,410 A * 12/1916 Van Tassel ............... G02C 1/04
 2/443
1,369,040 A * 2/1921 Malcom ................... G02C 5/02
 2/445
(Continued)

*Primary Examiner* — David D Davis
(74) *Attorney, Agent, or Firm* — J.C. Patents

(57) ABSTRACT

The present disclosure belongs to the field of intelligent wearing technology, and discloses an eye tracking apparatus and an eye tracking device, which are designed to improve the problem that the existing eye tracking apparatus based on a pupil-cornea reflection method is susceptible to ambient light interference. The eye tracking apparatus includes a mounting frame, an eye tracking component and a hood, and the mounting frame is configured to be connected with a head-mounted apparatus; the eye tracking component and the hood are disposed on the mounting frame, and the hood is capable of providing an enclosure between the mounting frame and a face of a user. The eye tracking device includes a head-mounted apparatus and the above eye tracking apparatus. The eye tracking apparatus and the eye tracking device of the present disclosure are used for achieving eye tracking.

17 Claims, 14 Drawing Sheets

(51) Int. Cl.
*G02B 27/00* (2006.01)
*G06K 9/00* (2006.01)

(52) U.S. Cl.
CPC ..... *G02B 27/0172* (2013.01); *G06K 9/00604* (2013.01); *G02B 2027/0138* (2013.01); *G02B 2027/0178* (2013.01)

(58) Field of Classification Search
CPC . G02B 2027/0178; A61B 3/113; A61B 3/152; G06K 9/00604; G06F 3/013
See application file for complete search history.

(56) References Cited

U.S. PATENT DOCUMENTS

| | | | | |
|---|---|---|---|---|
| 1,547,040 A * | 7/1925 | Humphrey | | A61F 9/025 2/441 |
| 1,651,488 A * | 12/1927 | Tully | | A61F 9/025 2/441 |
| 5,093,940 A * | 3/1992 | Nishiyama | | A61F 9/02 2/441 |
| 2009/0276942 A1* | 11/2009 | Chiang | | A63B 33/002 2/452 |
| 2012/0235902 A1* | 9/2012 | Eisenhardt | | G06F 3/012 345/156 |
| 2013/0114850 A1* | 5/2013 | Publicover | | H04N 5/247 382/103 |
| 2013/0222235 A1* | 8/2013 | Abdollahi | | G09G 5/006 345/156 |
| 2016/0062454 A1* | 3/2016 | Wang | | G09G 5/003 345/633 |
| 2016/0180591 A1* | 6/2016 | Shiu | | G06F 3/013 345/633 |
| 2017/0094816 A1* | 3/2017 | Yun | | H05K 5/03 |
| 2017/0102549 A1* | 4/2017 | Lee | | G02B 27/0172 |
| 2018/0032133 A1* | 2/2018 | Cho | | G06F 3/013 |
| 2019/0138094 A1* | 5/2019 | Miettinen | | G06K 9/00604 |

\* cited by examiner

EYE TRACKING APPARATUS AND EYE TRACKING DEVICE FOR THE ESTIMATION OF LINE-OF-SIGHT AND/OR GAZE POINT OF EYES

CROSS-REFERENCE TO RELATED APPLICATIONS

This application claims priority to Chinese Patent Application No. 201910477708.9, filed on Jun. 3, 2019, which is hereby incorporated by reference in its entirety.

TECHNICAL FIELD

The present disclosure relates to the field of intelligent wearable technology and, in particular, to an eye tracking apparatus and an eye tracking device.

BACKGROUND

Eye tracking, also known as line-of-sight tracking, is a technique for estimating line-of-sight and/or gaze point of eyes by measuring eye movement. The line-of-sight may be understood as a three-dimensional vector, and the gaze point may be understood as a two-dimensional coordinates of a certain plane onto which the three-dimensional vector projects. Currently a widely used optical recording method is: recording eye movement of a user by a camera or a camcorder (i.e. obtaining eye images reflecting the eye movement), and then extracting eye features from the obtained eye images to build a model for estimating line-of-sight/gaze point. Where, the eye features may include: a pupil position, a pupil shape, an iris position, an iris shape, an eyelid position, a canthus position, a glint (also referred to as a Purkinje image) position, and the like. In the optical recording method, the most popular eye tracking method is called pupil-cornea reflection method, and the principle of this method is that a light source is directed to an eye of a user, and a reflection point formed on a cornea of the user by the light source is called a glint (also referred to as a Purkinje image), where said glint refers to imaging presentation of an intense virtual image of a designated light source on the cornea of the user which may be captured by a sensor of a camera, the eye is photographed by an image acquisition device, thereby obtaining an eye image with the glint. When the eye moves, a relative position relationship between a center of a pupil and the glint changes correspondingly, and several eye images with glints acquired by the image acquisition device reflect a corresponding pupil/glints position change relationship, and the estimation of line-of-sight/gaze point may be performed according to the relative position change relationship.

However, the problem in the pupil-cornea reflection method is that complex ambient light tends to form unwanted glints on the cornea, where the unwanted glints refer to bright spots formed by other light sources other than the designated light source, thereby affecting extraction and judgment of normal glints, resulting in imprecise or inaccurate estimation of line-of-sight and gaze point.

SUMMARY

Embodiments of the present disclosure are to provide an eye tracking apparatus to improve the problem that an existing eye tracking apparatus based on the pupil-cornea reflection method is susceptible to ambient light interference.

To achieve the above objective, the present disclosure employs the following technical solutions.

An eye tracking apparatus configured to be used with a head-mounted apparatus, including a mounting frame, an eye tracking component and a hood, and the mounting frame is configured to be connected with the head-mounted apparatus, the eye tracking component and the hood are disposed on the mounting frame, and the hood is capable of providing an enclosure between the mounting frame and a face of a user.

Preferably the mounting frame includes a first frame and a second frame that are connected to each other, and the first frame and the second frame are respectively opposite to one eye of the user.

In one embodiment, the eye tracking apparatus may include one or more eye tracking components, preferably includes two eye tracking components, and each of the eye tracking components is disposed on the first frame and the second frame, respectively.

Preferably the hood may be configured to use in an outdoor environment or in a place where ambient light is sophisticated, the hood includes a first hood and a second hood, and the first hood is disposed on the first frame and is capable of providing an enclosure between the first frame and the face of the user; the second hood is disposed on the second frame and capable of providing an enclosure between the second frame and the face of the user.

Preferably at least one of the first hood and the second hood includes a connection frame and a hood body disposed on the connection frame, and the connection frame is connected with the mounting frame.

Preferably one of the connection frame and the mounting frame is provided with a plug pin/plug pins, and the other is provided with a plug hole/plug holes, the plug pin is pluggable into the plug hole.

Preferably the hood body includes a first portion and a second portion, which are distributed along a circumferential direction of the connection frame, and the first portion is overlapped with the second portion; a size of an overlapped area of the first portion and the second portion is adjustable.

Preferably the hood body is a hood body capable of generating a reversible deformation when being subjected to a force.

Preferably the eye tracking apparatus includes at least one lens for blocking interferential light, and the lens is disposed in the mounting frame or the connection frame. Alternatively, the eye tracking apparatus may include no lens.

Preferably the mounting frame is detachably connected with the head-mounted apparatus.

Preferably the mounting frame is provided with a connection member connecting with the head-mounted apparatus, and the connection member is detachably connected with the mounting frame; the mounting frame is provided with a connection control component for controlling whether the connection member is connected with the mounting frame.

Preferably the connection control component includes an operation portion, a reset portion, and a sliding portion, all of which are disposed on the mounting frame; one end of the sliding portion is connected with the operation portion, and the other end is connected with the connection member; the sliding portion is capable of being connected with or disengaged from the connection member under the driving of the operation portion; the reset portion causes the sliding portion to always have a tendency of moving towards a position where the sliding portion is connected with the connection member.

Preferably the mounting frame includes an inner casing and an outer casing which are mutually interlocked to form a receiving cavity, and the outer casing is provided with a mounting groove protruding in a direction away from the inner casing, and the operation portion is inserted into the mounting groove and movable relative to the mounting groove to be close to or away from a groove bottom of the mounting groove; the reset portion is disposed between the groove bottom of the mounting groove and the operation portion, and the sliding portion is disposed in the receiving cavity.

Preferably the connection member is located at a side of the mounting frame away from the hood, and includes a substrate, a first connection portion disposed at one end of the substrate and a second connection portion disposed on a side of the substrate away from the first connection portion, the first connection portion is configured to be connected with the head-mounted apparatus, and the second connection portion is configured to pass through the outer casing to be connected with the sliding portion.

Preferably a positioning protrusion is disposed at a side of the substrate towards the outer casing, and a positioning groove corresponding to the positioning protrusion is disposed on the outer casing; or the positioning groove is disposed at the side of the substrate towards the outer casing, and the positioning protrusion corresponding to the positioning groove is disposed on the outer casing.

Preferably the sliding portion includes a sliding plate, and the sliding plate is provided with a third connection portion corresponding to the second connection portion, and when the connection control component is in a first state, the third connection portion is cooperated with the outer casing to snap with the connection member to fix the connection member; when the connection control component is in a second state, a position of the third connection portion relative to the outer casing is changed, and the fixing of the connection member is released.

Preferably the second connection portion includes a hook, and the third connection portion includes a long hole, and the hook can pass through the outer casing and move along an extending direction of the long hole.

Preferably the sliding plate is provided with a guiding groove, and a guiding block matching the guiding groove is disposed on a side of the outer casing towards the inner casing.

Preferably a limiting platen is disposed on a side of the guide block away from the outer casing, and the sliding plate is located between the limiting platen and the outer casing, and is capable of abutting against the limiting platen and moving relative to the limiting platen.

Preferably the eye tracking component includes at least one light source and at least one image acquisition component, and the light source and the image acquisition component are disposed on the mounting frame. The image acquisition component is preferably disposed at a position of the mounting frame above or below the eyes of the user for the best acquisition of eye images. Preferably, the eye tracking component includes a plurality of light sources, the light sources are configured to form basically evenly distributed glints on a pupil of the user.

Specifically the light sources include at least one, which may be an infrared light source or visible light, and the light sources may irradiate on one eye of the user. The image acquisition component includes at least one camera, and the one camera may be configured to capture eye images of the user; the image acquisition component may also include at least two cameras, each of which may be configured to capture at least part images of the eye of the user.

Preferably the eye tracking apparatus further includes a scene camera for acquiring a scene image, and the scene camera is disposed on the mounting frame and can capture a view image seen by the user, and the view image may be a still image and/or a video image and/or other image data. The scene camera is configured to be cooperated with the image acquisition component to determine a gaze position of the eye of the user in a usage scene.

The beneficial effects of the present disclosure are as follows:

The eye tracking apparatus provided by the present disclosure is configured to be used with a head-mounted apparatus, and includes a mounting frame configured to connect with the head-mounted apparatus, and an eye tracking component, and a hood that are disposed on the mounting frame. After the eye tracking apparatus is connected to the head-mounted apparatus and the user correctly wears the head-mounted apparatus, the hood is capable of providing an enclosure between the mounting frame and a face of the user, reducing ambient light entering from a gap between the mounting frame and the face of the user, thereby reducing interference of the ambient light on the eye tracking component.

The embodiments of the present disclosure are also to provide an eye tracking device to improve the problem that an existing eye tracking apparatus based on the pupil-cornea reflection method is susceptible to ambient light interference.

To achieve the above objection, the present disclosure employs the following technical solutions.

An eye tracking device, including a head-mounted apparatus and the eye tracking apparatus described as above.

The eye tracking device provided by the present disclosure includes the eye tracking apparatus described as above, and is capable of achieving the beneficial effects that the eye tracking apparatus can achieve, which will not be repeatedly described herein.

BRIEF DESCRIPTION OF THE DRAWINGS

To describe the technical solutions in embodiments of the present disclosure more clearly, the following briefly introduces the accompanying drawings needed for describing the embodiments of the present disclosure. Apparently, the accompanying drawings in the following description are merely some embodiments of the present disclosure, and persons of ordinary skill in the art may still derive other drawings from the contents of the embodiments of the present disclosure and these accompanying drawings without creative effort.

In the drawings.

Figure 1:
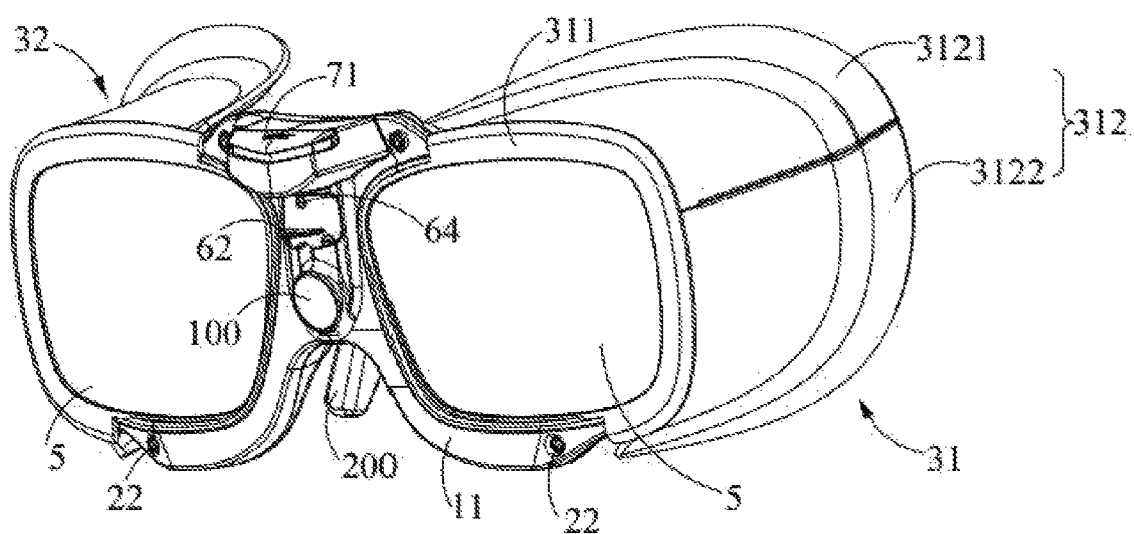
FIG. 1 is a schematic structural diagram of an eye tracking apparatus at a first angle provided by the present disclosure.
Figure 2:
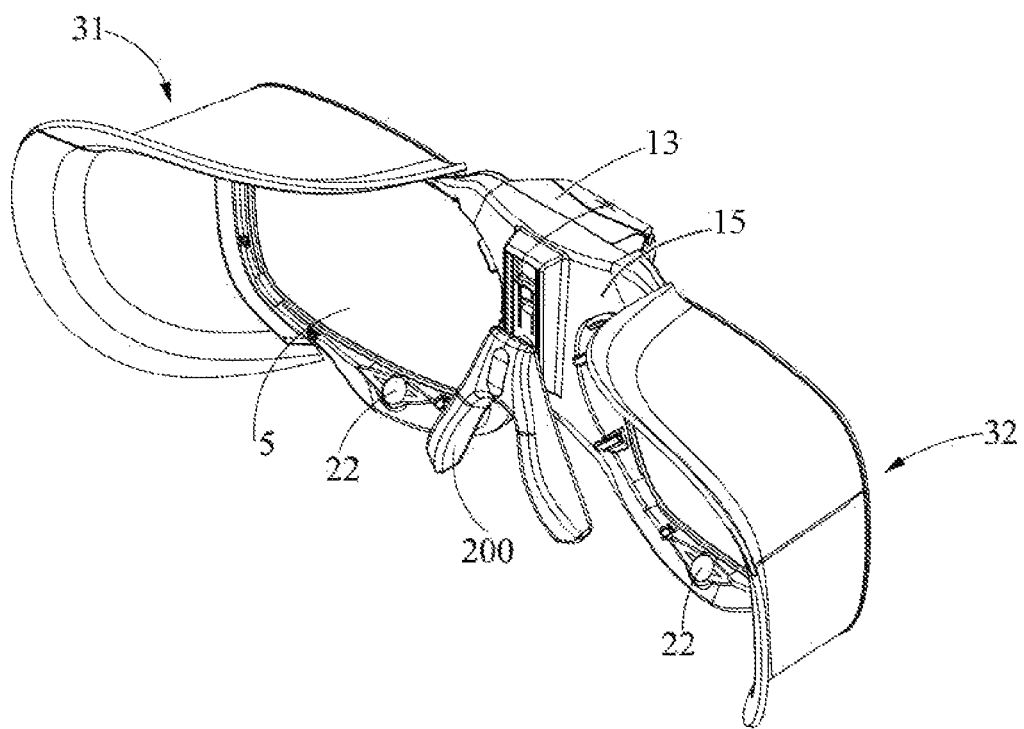
FIG. 2 is a schematic structural diagram of an eye tracking apparatus at a second angle provided by the present disclosure.

1—mounting frame; 11—first frame; 12—second frame; 13—outer casing; 15—inner casing; 131—guiding block; 132—mounting groove; 1321—groove bottom; 14—pressing portion; 2—eye tracking component; 21—light source; 22—image acquisition component; 3—hood; 31—first hood; 32—second hood; 311—connection frame; 312—hood body; 3121—first portion; 3122—second portion; 4—plug pin; 5—lens; 6—connection member; 61—substrate; 62—first connection portion; 63—second connection portion; 64—curved support portion; 7—connection control component; 71—operation portion; 72—reset portion; 73—sliding plate; 731—third connection portion; 732—guiding groove; 74—sliding portion; 8—limiting platen; 100—scene camera; 200—nose pad.

DESCRIPTION OF EMBODIMENTS

The present disclosure will be further described in detail below with reference to the accompanying drawings and embodiments. It is understood that the specific embodiments described herein are merely illustrative of present disclosure and are not intended to limit present disclosure. It should also be noted that, for ease of description, only a part structure rather than overall structure related to the present disclosure are shown in the drawings.

In the description of the present disclosure, unless otherwise specifically specified and defined, the terms "connected", "connection", and "fixed" are to be understood broadly, and may be, for example, a fixed connection, a detachable connection, or an integral, and may be a mechanical connection or an electrical connection, and may be direct connection or indirect connection through an intermediate medium, and may be an internal connection of two elements or the interaction of two elements. For those skilled in the art, specific meanings of the above terms in the present disclosure may be understood in specific situations.

In the description of the present embodiments, orientation or positional relationship, such as the terms "upper", "lower", "right" and the like, is based on the orientation or positional relationship shown in the drawings, and is merely for convenience of description and simplification of operation, and does not indicate or imply that the indicated apparatus or component must has a specific orientation or be constructed and operated in a specific orientation, therefore it cannot be understood as limiting the present disclosure.

Moreover, the terms "first" and "second" are merely used to make distinction in the description and have no special meanings.

The terms "apparatus" and "device" are used to make distinction in the description, and these two terms may be used interchangeably.

Referring to FIG. 1 to FIG. 4, an eye tracking apparatus provided by an embodiment includes a mounting frame 1, an eye tracking component 2 and a hood 3, the mounting frame 1 is configured to be connected with a head-mounted apparatus, the eye tracking component 2 and the hood 3 are disposed on the mounting frame 1, and the hood 3 is capable of providing an enclosure between the mounting frame 1 and a face of a user.

After the eye tracking apparatus is connected with the head-mounted apparatus and the user correctly wears the head-mounted apparatus, the hood 3 is capable of providing an enclosure between the mounting frame 1 and the face of the user, reducing ambient light entering from a gap between the mounting frame 1 and the face of the user, thereby reducing interference of the ambient light on the eye tracking component 2.

In order to achieve a better shading effect and more advantageously reduce the interference of the ambient light on the eye tracking component 2, preferably the hood 3 may attach onto the face of the user.

The head-mounted apparatus in embodiments may be a pair of glasses or a spectacle frame, but is not limited to the above two cases, and the embodiment gives an example that the head-mounted apparatus is a pair of glasses or a spectacle frame to illustrate. In addition, the eye tracking apparatus may be connected to a side of the head-mounted apparatus away from the face of the user, or may be disposed at a side of the head-mounted apparatus towards the face of the user. The embodiment gives an example that the eye tracking apparatus is located at the side of the head-mounted apparatus towards the face of the user to illustrate.

Figure 4:
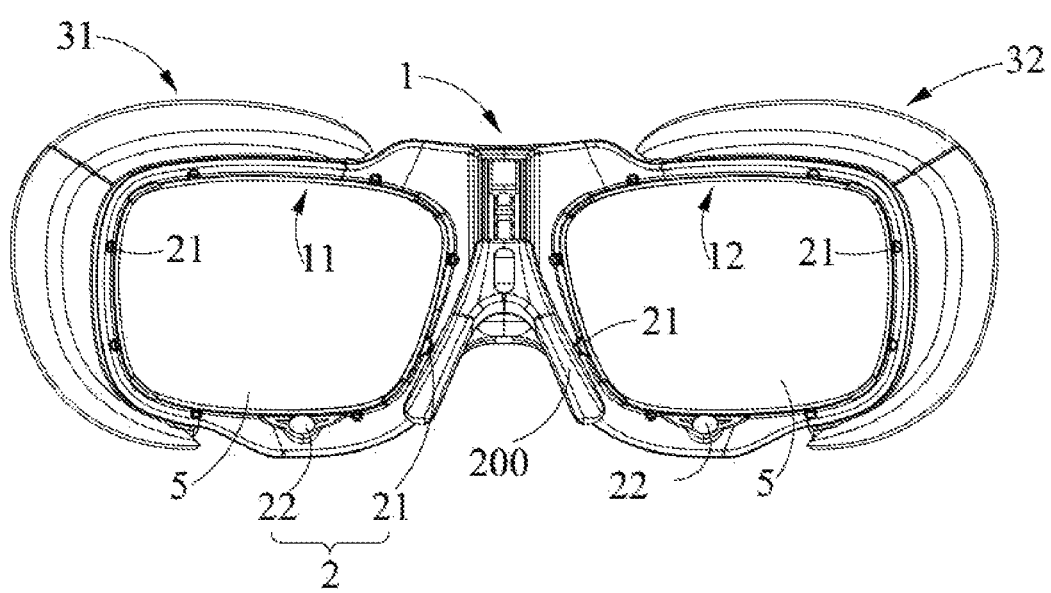
FIG. 4 is a rear view of an eye tracking apparatus provided by the present disclosure.

Referring to FIG. 4, in order to make the eye tracking apparatus more fit with the user's usage habits, optionally in some embodiments, the mounting frame 1 includes a first frame 11 and a second frame 12 that are connected to each other, and the first frame 11 and the second frame 12 are respectively opposite to one eye of the user. Specifically, the first frame 11 and the second frame 12 may be connected by a beam. Of course, in order to facilitate processing and assembling, the mounting frame 1 also may be of a large single frame structure. Further, one eye tracking component 2 may be disposed on the first frame 11, and another eye tracking component 2 may be disposed on the second frame 12.

Taking the mounting frame 1 including the first frame 11 and the second frame 12 as an example, at this time, for convenience of processing, the hood 3 may be of an integral structure that provides an enclosure between the first frame 11, the second frame 12 and the face of the user. Preferably, referring to FIG. 1 to FIG. 6, in order to better attach onto the face of the user, the hood 3 may be of a separate structure, for example, the hood 3 includes a first hood 31 disposed on the first frame 11 and a second hood 32 disposed on the second frame 12. After the eye tracking apparatus is connected with the head-mounted apparatus and the user correctly wears the head-mounted apparatus, the first hood 31 is capable of providing an enclosure between the first frame 11 and the face of the user, reducing ambient light entering from a gap between the first frame 11 and the face of the user. The second hood 32 is capable of providing an enclosure between the second frame 12 and the face of the user, reducing ambient light entering from a gap between the second frame 12 and the face of the user. In order to achieve a better shading effect, it is preferable that both of the first hood 31 and the second hood 32 are capable of attaching onto the face of the user.

Figure 5:
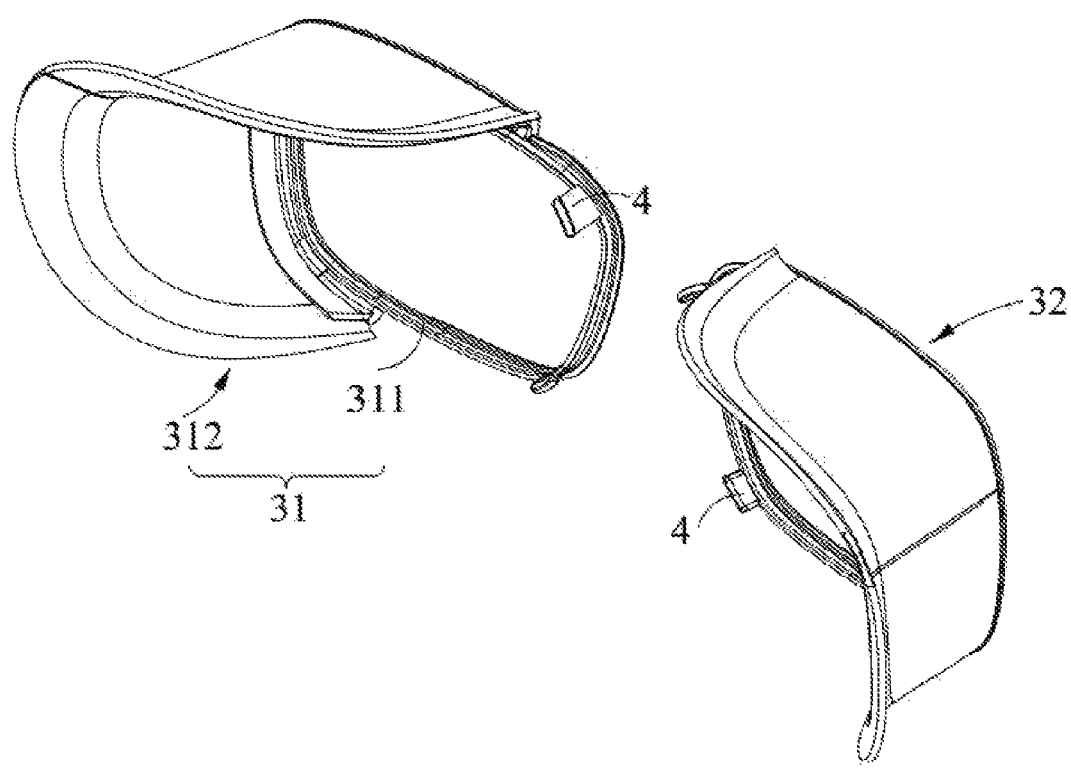
FIG. 5 is an axonometric drawing of a first hood and a second hood in an eye tracking apparatus provided by the present disclosure.
Figure 6:
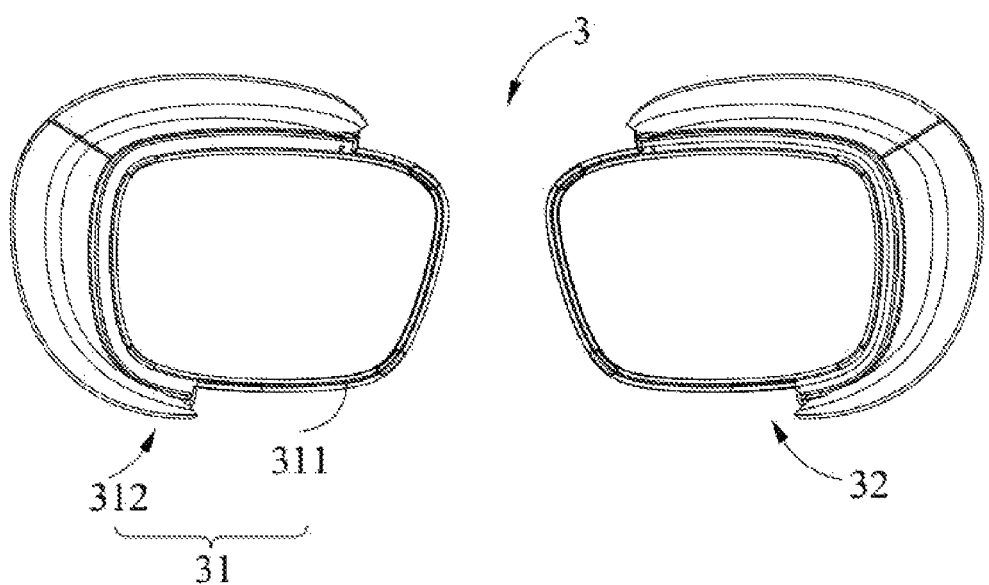
FIG. 6 is a rear view of a first hood and a second hood in an eye tracking apparatus provided by the present disclosure.

Further, taking the hood 3 including the first hood 31 and the second hood 32 as an example, optionally referring to FIG. 1 and FIG. 5, the first hood 31 and the second hood may each include a connection frame 311 and a hood body 312 disposed on the connection frame 311 (specifically, the connection frame 311 may be bonded with the corresponding hood body 312), and the connection frame 311 is connected with the corresponding first frame 11 or the second frame 12. Of course, it may be that only one of the first hood 31 and the second hood 32 has the above structure.

Optionally the hood body 312 may be of a C-like structure. Further, an edge of the hood body 312 may be provided with a transition surface for attaching onto the face of the user to better block ambient light; the first hood 31 and the second hood 32 may be of a symmetrical structure.

The connection frame 311 may be pluggable into, bolted to or bonded to the mounting frame 1, and taking that the connection frame 311 is pluggable into the mounting frame 1 as an example, one of the connection frame 311 and the mounting frame 1 is provided with a plug pin/plug pins 4, and the other is provided with a plug hole/plug holes, the plug pin 4 is pluggable into the plug hole. Specifically, one of the first frame 11 and the corresponding connection frame 311 is provided with the plug pin/plug pins 4, and the other is provided with the plug hole/plug holes, and the connection between the connection frame 311 and the first frame 11 is implemented by plugging the plug pin 4 into the plug hole. Preferably, in order to make the connection between the first hood 31 and the first frame 11 more convenient, the plug pin 4 is disposed on the connection frame 311, and the plug hole is disposed on the first frame 11. Specifically, four plug pins 4 may be disposed at intervals on the connection frame 311. One of the second frame 12 and the corresponding connection frame is provided with plug pins, and the other is provided with plug holes, the plug pins are pluggable into the plug holes. Preferably, in order to make the connection between the second hood 32 and the second frame 12 more convenient, the plug pins are disposed on the connection frame, and the plug holes are disposed on the second frame 12. Specifically, four plug pins may be disposed at intervals on the connection frame.

Further, please continue to refer to FIG. 1, in order to make the eye tracking apparatus provided by the embodiment applies to users with different sizes of faces, and to make the hood 3 has good shading effect for different users, in other embodiments the hood body 312 may include a first portion 3121 and a second portion 3122 which are lapped along a circumferential direction of the connection frame 311. When sizes of the faces of the users are different, sizes of overlapped areas of the first portion 3121 and the second portion 3122 are different. Specifically, when the apparatus is used by a user with a wider face, the overlap between the first portion 3121 and the second portion 3122 is opened, and the overlapped area is small; when the apparatus is used by a user with a smaller face, the overlap between the first portion 3121 and the second portion 3122 remains as it is, and the overlapped area is large. Of course, in other embodiments, the hood body 312 may also be of an integral structure.

Optionally, in order to make the hood 3 better attaches onto the face of the user, and achieve a better shading effect on the whole, the hood body 312 is a hood body capable of generating a reversible deformation when being subjected to a force. Preferably, the hood body 312 may be a rubber (for example, thermoplastic polyurethane elastomer rubber) hood body or a plastic soft rubber hood body, and the like.

Optionally, at least one lens 5 for blocking interferential light is disposed in the mounting frame 1 or the connection frames 311 of the eye tracking apparatus provided by some embodiments. Obviously, the interferential light refers to light in ambient light that interferes with the performances of the eye tracking apparatus. Specifically, the light blocked by the lens 5 may be light in an environment with a wavelength as the same as the light emitted by a light source 21 in the eye tracking component 2. For example, when the light source 21 in the eye tracking component 2 is an infrared light source, the lens 5 may be an infrared cut-off filter.

As an alternative, in other embodiments, one of the following lenses may be mounted in the mounting frame 1 or the connection frame 311: a nearsighted lens, a farsighted lens, a sunglass lens, a plain glass lens, a lens through which single-band light passes or is blocked, etc.

Preferably the mounting frame 1 is detachably connected with the head-mounted apparatus, for example, being pluggable into, snapped to or threaded into the head-mounted apparatus, so that the eye tracking apparatus may be used with different head-mounted apparatuses to make the user experiences better.

Figure 3:
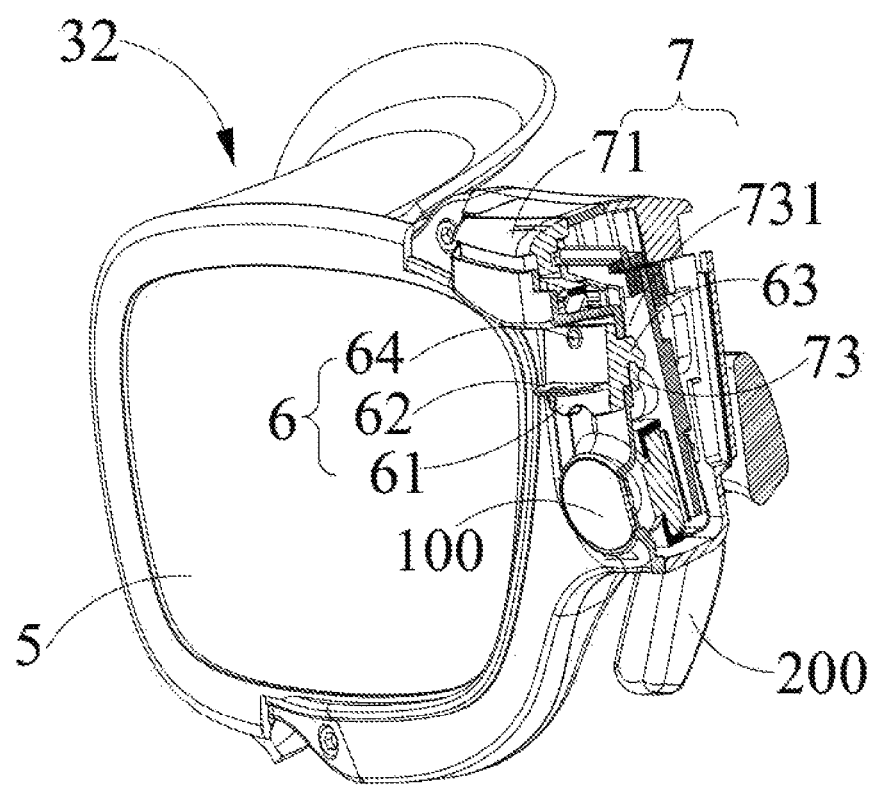
FIG. 3 is a schematic cross-sectional view of a partial structure of an eye tracking apparatus provided by the present disclosure.
Figure 11:
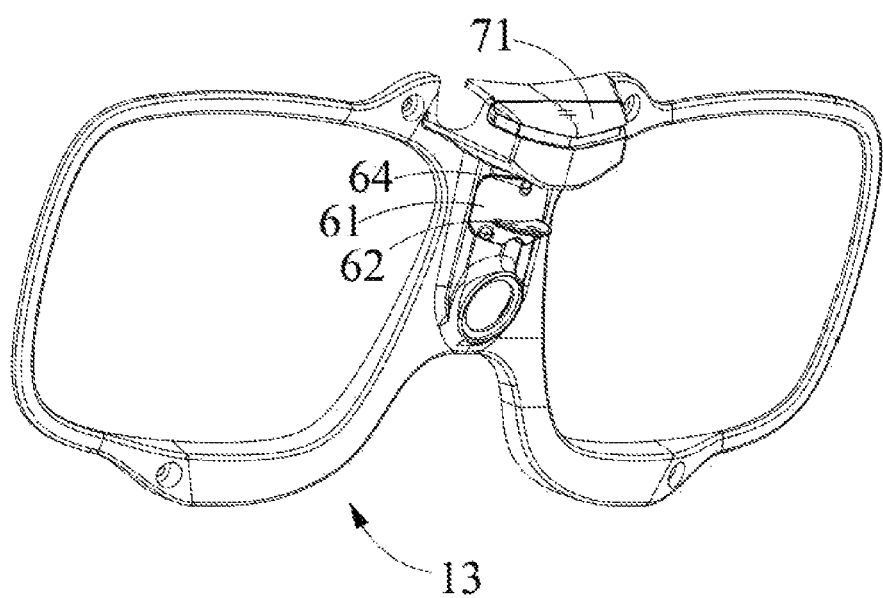
FIG. 11 is a schematic structural diagram of the eye tracking apparatus shown in FIG. 10 at another angle.

Specifically, referring to FIG. 1, FIG. 3 and FIG. 11, the mounting frame 1 may be provided with a connection member 6 connecting with the head-mounted apparatus, the connection member 6 being detachably connected with the mounting frame 1, the mounting frame 1 is provided with a connection control component 7 for controlling whether the connection member 6 is connected with the mounting frame 1. When the connection control component 7 is in a first state (the connection control component 7 is in the first state in FIGS. 1, 3, 10, and 12), the connection member 6 is connected with the mounting frame 1. When the connection control component 7 is in a second state, the connection between the connection member 6 and the mounting frame 1 is released. The connection member 6 is detachably connected with the mounting frame 1 and is used for connecting with the head-mounted apparatus at the same time. The connection between the connection member 6 and the mounting frame 1 may be released by changing the state of the connection control component 7 (that is, making the head-mounted apparatus to which the connection member 6 is connected separates from the mounting frame 1), so that the separation between the head-mounted apparatus and the eye tracking apparatus is more convenient.

Further, the connection control component 7 may include an operation portion 71, a reset portion 72, and a sliding portion 74, all of which are disposed on the mounting frame 1; one end of the sliding portion 74 is connected with the operation portion 71, and the other end is configured to be connected with the connection member 6. The sliding portion 74 is capable of being connected with or disengaged from the connection member 6 under the driving of the operation portion 71. The reset portion 72 causes the sliding portion 74 to always have a tendency of moving towards a position where the sliding portion 74 is connected with the connection member 6.

Specifically, referring to FIG. 1, FIG. 3, FIG. 8, FIG. 9, FIG. 10, FIG. 12 and FIG. 13, the mounting frame 1 includes an inner casing 15 and an outer casing 13 that are mutually interlocked, and the outer casing 13 is provided with a mounting groove 132 protruding in a direction away from the inner casing 15, and the operation portion 71 is inserted into the mounting groove 132 and is movable relative to the mounting groove 132 to be close to or away from a groove bottom 1321 of the mounting groove 132. Optionally, in the embodiment, the operation portion 71 moves up and down relative to the mounting groove 132. In other embodiments, a relative moving direction of the operation portion 71 and the mounting groove 132 depends on their location, for example, when the connection control component 7 is disposed horizontally, the operation portion 71 moves left and right relative to the mounting groove 132. The reset portion 72 is disposed between the groove bottom 1321 of the mounting groove 132 and the operation portion 71, and the sliding portion is disposed in a receiving cavity surrounded by the inner casing 15 and the outer casing 13.

The reset portion 72 may be an elastic reset member. For example, the reset portion 72 may be an elastic member of a W-shaped structure. One end of the elastic member abuts against the bottom end of the operation portion 71, and the other end abuts against the groove bottom 1321 of the mounting groove 132. Further, in order to prevent the elastic member from moving up and down to make the performances of the connection control unit 7 more stable, the mounting groove 132 is provided with a pressing portion 14 for pressing a connection end of the elastic member.

Preferably, referring to FIG. 3, the connection member 6 is located at a side of the mounting frame 1 away from the hood 3. The connection member 6 includes a substrate 61, a first connection portion 62 disposed at one end of the substrate 61, and a second connection portion 63 disposed on a side of the substrate 61 away from the first connection portion 62. The first connection portion 62 is configured to be connected with the head-mounted apparatus, and the second connection portion 63 is configured to pass through the outer casing 13 (the outer casing 13 is provided with an escape hole through which the second connection portion 63 passes) to be connected with the sliding portion 74.

Further, the sliding portion 74 includes a sliding plate 73, and the sliding plate 73 is provided with a third connection portion 731 corresponding to the second connection portion 63, and when the connection control component 7 is in the first state, the third connection portion 731 is cooperated with the outer casing 13 to snap with the connection member 6 to fix the connection member 6; when the connection control component 7 is in the second state, a position of the third connection portion 731 relative to the outer casing 13 is changed, and the fixing of the connection member 6 is released.

Optionally, the second connection portion 63 includes a hook, and the third connection portion 731 includes a long hole, and the hook may stick into the long hole through passing the escape hole on the outer casing 13. When the operation portion 71 moves under the action of an external force, the slide plate 73 can move relative to the hook (that is, the relative position of the long hole and the hook may be changed). Specifically, two hooks may be disposed side by side on the substrate 61, and upper long holes of the sliding plate 73 are in one-to-one correspondence with the hooks.

Preferably, in order to position the connection member 6 on the outer casing 13 so as to facilitate the mounting of the connection member 6, a positioning protrusion may be disposed at a side of the substrate 61 towards the outer casing 13, and a positioning groove corresponding to the positioning protrusion may be disposed on the outer casing 13; or, the positioning groove is disposed at the side of the substrate 61 towards the outer casing 13, and the positioning protrusion corresponding to the positioning groove is disposed on the outer casing 13.

In addition, a curved support portion 64 may be disposed at an end of the substrate 61 away from the face of the user for supporting a curved portion of the beam of the spectacle frame, so as to make the relative position between the eye tracking apparatus and the spectacle frame more stable, thereby ensuring stability of the performances of the eye tracking apparatus.

The connection member 6 is configured to be connected with the head-mounted apparatus, and taking that the head-mounted apparatus is a pair of glasses or a spectacle frame as an example, the first connection portion 62 may be a plug plate provided with a first connection hole, a slot matching the plug plate is disposed on the beam of the spectacle frame, an upper wall of the slot is provided with a second connection hole corresponding to the first connection hole, and a lower wall of the slot is provided with a third connection hole corresponding to the first connection hole. The second connection hole is a light hole, and one of the first connection hole and the third connection hole is a threaded hole, and the other is a light hole. Preferably, the first connection hole is a light hole, and the third connection hole is a threaded hole. The plug plate is inserted into the slot, and a bolt passes through, in turn from bottom to top, the third connection hole, the first connection hole and the second connection hole, and locks the relative position of the connection member 6 and the beam of the spectacle frame. Of course, the plug plate may also be snapped to, screwed into or riveted to the beam of the spectacle frame.

Figure 7:
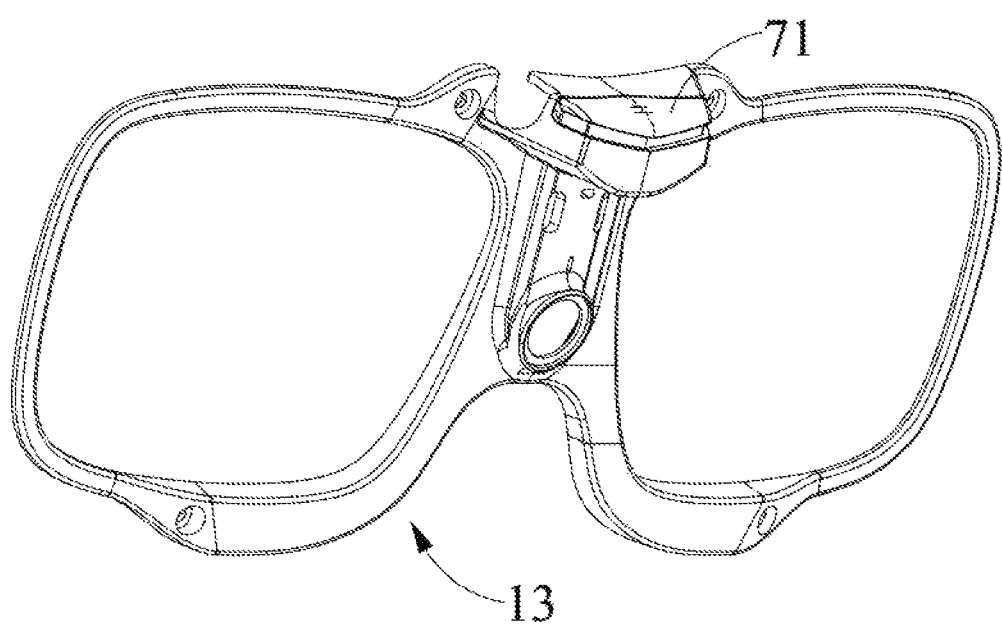
FIG. 7 is a schematic diagram of a partial structure of an eye tracking apparatus provided by the present disclosure.
Figure 12:
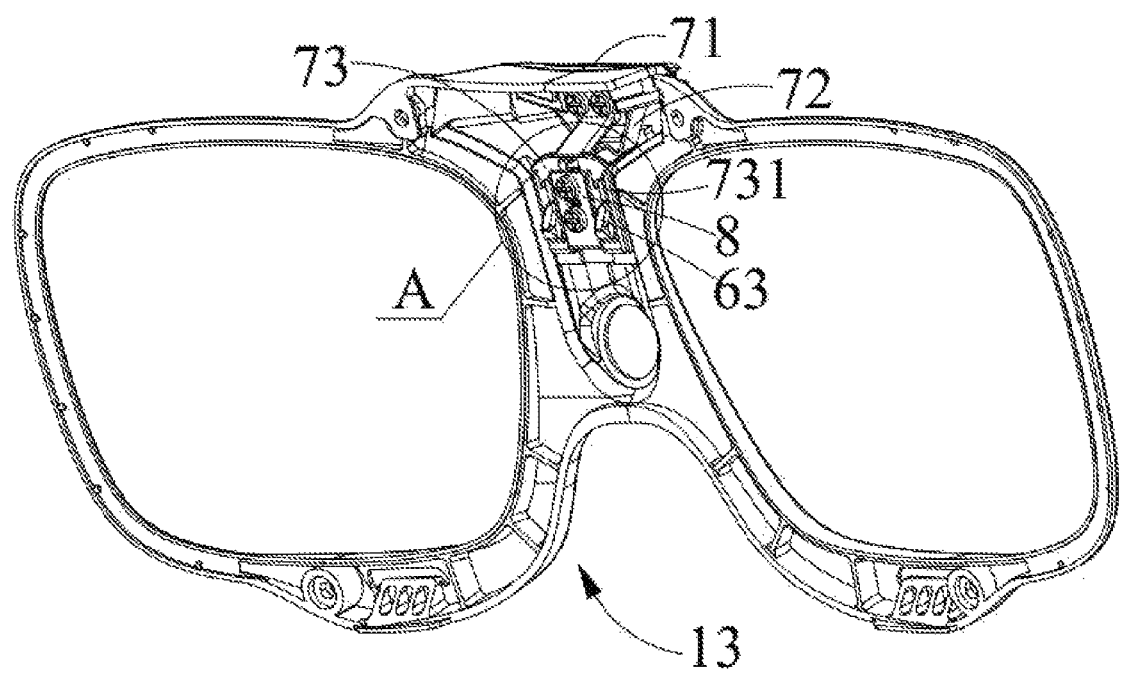
FIG. 12 is a schematic diagram of a partial structure of an eye tracking apparatus provided by the present disclosure.
Figure 13:
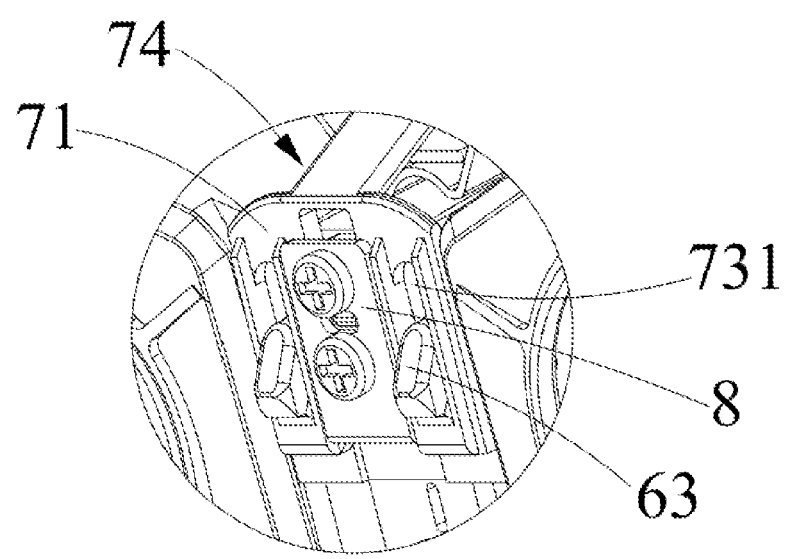
FIG. 13 is an enlarged view of A of FIG. 12.

Referring to FIG. 3, FIG. 7, and FIG. 12, the operation portion 71 may be a button. When the connection control component 7 is in the first state, the button is in a state of being lifted by the reset portion 72, and the sliding portion 74 is cooperated with the outer casing 13 to fix the connection member 6 onto the outer casing 13. When the button is pressed down, the button drives the sliding portion 74 to move downward relative to the outer casing 13, and the long hole on the sliding plate 73 no longer supports the hook on the connection member 6, at this time, pulling the connecting member 6 or the head-mounted apparatus in a direction away from the face of the user can make the connection member 6 together with the head-mounted apparatus separate from the mounting frame 1, thereby achieving separation of the eye tracking apparatus and the head-mounted apparatus.

Figure 8:
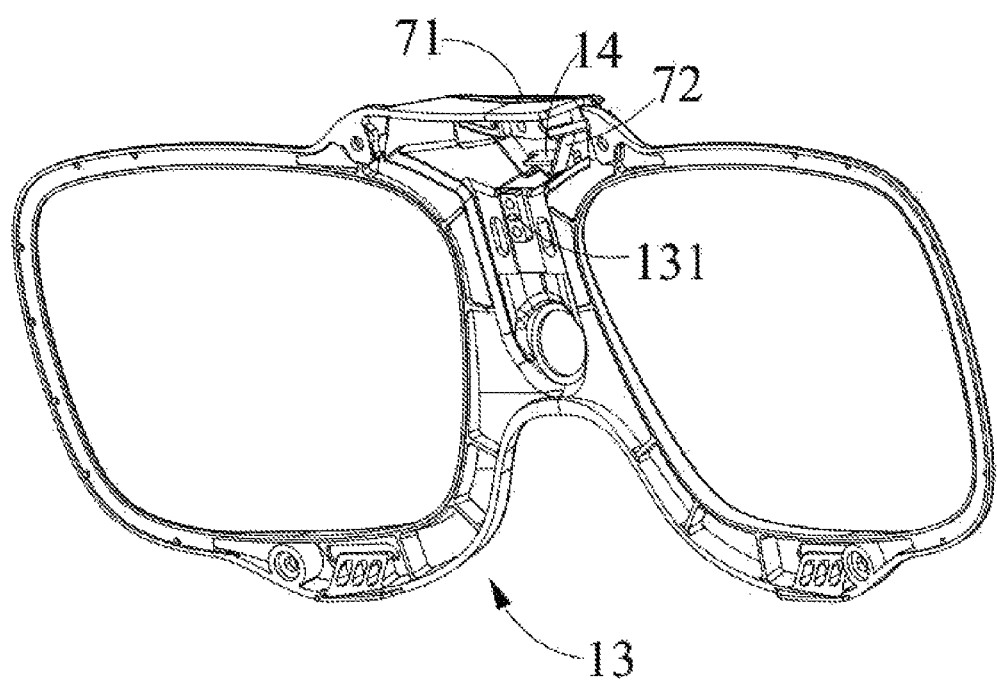
FIG. 8 is a schematic structural diagram of the eye tracking apparatus shown in FIG. 7 at another angle.
Figure 9:
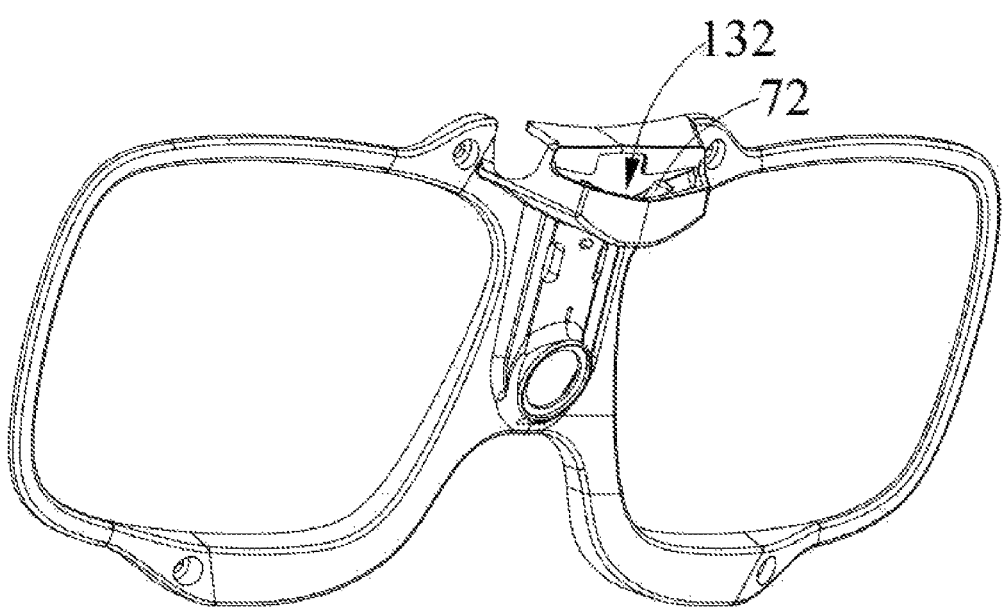
FIG. 9 is a schematic structural diagram of an outer casing of an eye tracking apparatus provided by the present disclosure.
Figure 10:
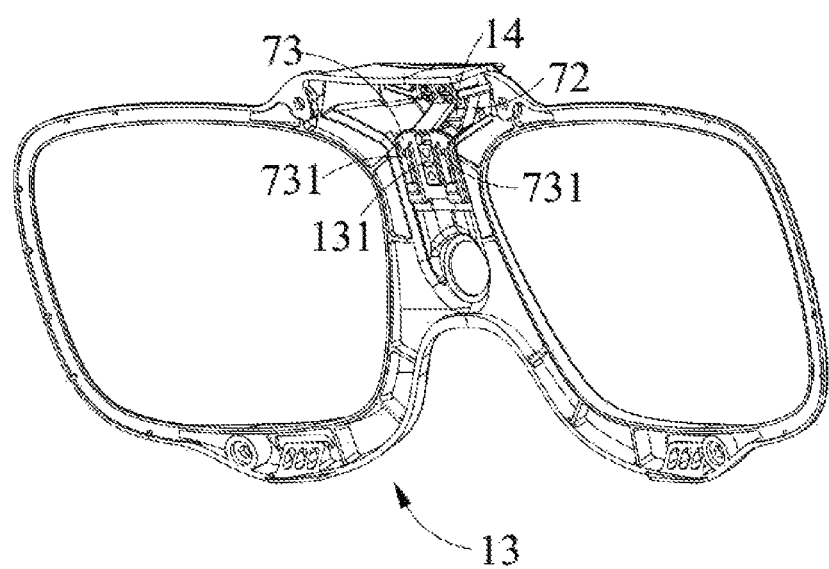
FIG. 10 is a schematic diagram of a partial structure of an eye tracking apparatus provided by the present disclosure.
Figure 14:
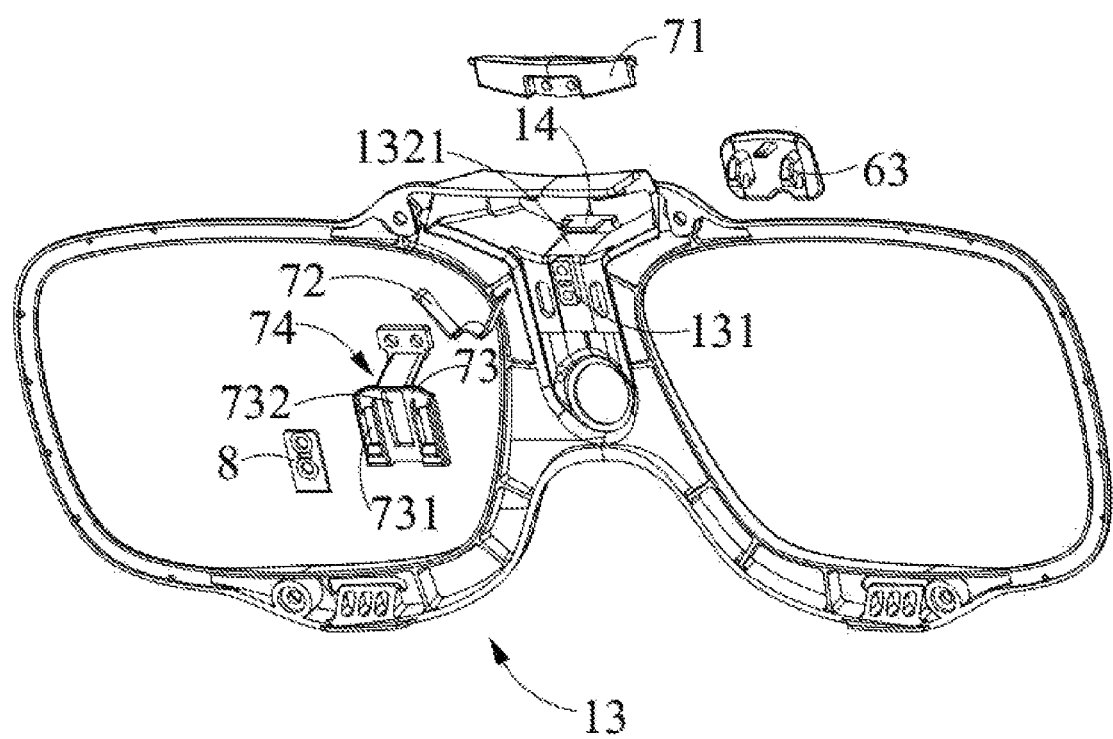
FIG. 14 is an exploded view of the eye tracking apparatus shown in FIG. 12.

Referring to FIG. 8 and FIG. 14, in order to make the movement of the sliding portion 74 more reliable, a guiding groove 732 may be disposed on the sliding plate 73, and a guiding block 131 matching with the guiding groove 732 may be disposed at a side of the outer casing 13 towards the inner casing 15. The guide block 131 is inserted into the guide groove 732 and can slide relative to the guide groove 732 to guide the movement of the sliding portion 74.

Preferably the outer casing 13 may be provided with a limiting groove for mounting the sliding portion 74, and the limiting groove can not only facilitate the mounting of the sliding portion 74, but also function of guiding and limiting the movement of the sliding portion 74.

Further, in order to limit the position of the sliding plate 73 in a direction perpendicular to the face of the user, a limiting platen 8 may be disposed at a side of the guiding block 131 away from the outer casing 13, so that the sliding plate 73 is located between the limiting platen 8 and the outer casing 13 and can abut against the limiting platen 8 and move relative to the limiting platen 8.

Preferably, a nose pad 200 may be disposed at a side of the inner casing 15 towards the face of the user, and the nose pad 200 has a figure-eight shape. After the eye tracking apparatus is connected with the head-mounted apparatus and the user correctly wears the head-mounted apparatus, the nose pad 200 may be placed on the bridge of the nose of the user and function as a support.

Preferably, the eye tracking component 2 includes one or more light sources 21 and one or more image acquisition components 22, and the light sources 21 and the image acquisition components 22 are disposed on the mounting frame 1. The eye tracking apparatus may illuminate an eye of the user through the light sources 21 of the eye tracking component 2 and glints are formed on a cornea of the eye of the user, and the image acquisition components 22 of the eye tracking component 2 acquire glint position information and pupil position information, thereby acquiring eye data of the user, the estimation of line-of-sight and/or gaze point of the eye of the user is calculated by a plurality of glint position information and pupil position information. Similarly, when the eye tracking apparatus includes two or more eye tracking components 2, the eye tracking apparatus may illuminate two eyes of the user through light sources 21 of the eye tracking components 2, and glints are formed on corneas of the eyes of the user, and image acquisition components 22 of the eye tracking components 2 may acquire glint position information and pupil position information, thereby acquiring eye data of both two eyes of the user, respectively. Specifically, the light sources 21 of the eye tracking component 2 include at least one, which may be an infrared light source or visible light, and the light sources 21 of the eye tracking component 2 may illuminate one eye of the user, similarly, the light sources 21 of another eye tracking component 2 may illuminate another eye of the user. The light sources 21 may include infrared illuminators capable of emitting infrared light, as it will be readily understood by persons of ordinary skill in the art, other illuminators however may be used, including illuminators that emit ultraviolet and/or visible light.

Optionally, the first frame 11 and the second frame 12 may be provided with 1 to 8 light sources 21, preferably 5, 6, 7 or 8 light sources 21.

The image acquisition component 22 includes at least one camera, and the one camera may be configured to capture images of a corresponding eye of the user; the image acquisition component may also include at least two cameras, for example, a lower frame of the first frame 11 and a lower frame of the second frame 12 are provided with at least one camera respectively, and each camera may be configured to capture at least part images of the eyes of the user, where the at least part images refer to images of a corresponding eye of the user. In one embodiment, the first frame 11 and the second frame 12 are provided with two cameras, respectively, and these cameras may be disposed on positions of the first frame 11 and the second frame 12 where images of the eyes of the user could be captured, for example disposed on top and/or bottom borders of the first frame 11 and the second frame 12, respectively. Further, in order to prevent the influence of ambient light on the camera, a light filter may be disposed on the camera.

In other embodiments, a wavelength filter may be used in conjunction with the camera to filter out optical wavelengths that do not correspond to the wavelengths emitted by the light source 21. For example, in the case where the light source 21 emits infrared light, a filter that only makes infrared light to pass through the camera may be used. In this way, the camera may only detect flicker caused by the light emitted by the light source 21.

The eye tracking apparatus further includes a scene camera 100 for acquiring a scene image. The scene camera 100 is disposed on the mounting frame 1 and may capture a view image seen by the user, and the view image may be a still image and/or a video image and/or other image data. The scene camera 100 may be cooperated with the image acquisition component 22 to determine a gaze position of eyes of the user in an usage scene.

Optionally the scene camera 100 may be disposed in a cavity enclosed by the inner casing 15 and the outer casing 13 and is located at a middle portion of the mounting frame in height, and between the first frame 11 and the second frame 12; more specifically, the scene camera 100 may be located under the beam of the spectacle frame, and a lens of the scene camera 100 aligns with, lower than or protrudes from the outer casing 13 to prevent the head-mounted apparatus from blocking the shooting of the scene camera.

The eye tracking apparatus may analyze an element in images or videos captured by the scene camera 100 to determine orientation of a head of the user and movement speed of the head of the user. By analyzing a relative position of the element in the continuous images or videos, adjustment to the calculation of a gaze direction may be done to compensate for the movement.

It should be noted that "above", "below", "inner", "outer" and the like mentioned in the embodiments refer to orientations in the case after the eye tracking apparatus is correctly connected with the head-mounted apparatus and the user normally wears the head-mounted apparatus. The "inner" is the side close to the face of the user, and "outer" is the side away from the face of the user.

The eye tracking device provided by the embodiments includes a head-mounted apparatus and the eye tracking apparatus described as above.

It is apparent that the above-described embodiments of the present disclosure are merely illustrative of the present disclosure and are not intended to limit the embodiments of the present disclosure. For persons of ordinary skill in the art, various obvious changes, modifications and substitutions may be made without departing from the protection scope of the present disclosure. There is no need and no way to exhaust all the embodiments. Any modification, equivalent substitution and improvement made within the spirit and principle of the present disclosure are intended to be included within the protection scope of the claims of the present disclosure.

The invention claimed is:

1. An eye tracking apparatus configured to be used with a head-mounted apparatus, comprising a mounting frame (1), an eye tracking component (2) and a hood (3), and the mounting frame (1) is configured to be connected with the head-mounted apparatus, the eye tracking component (2) and the hood (3) are disposed on the mounting frame (1), and the hood (3) is capable of providing an enclosure between the mounting frame (1) and a face of a user, wherein the mounting frame (1) is detachably connected with the head-mounted apparatus, and the mounting frame (1) is provided with a connection member (6) connecting with the head-mounted apparatus, the connection member (6) being detachably connected with the mounting frame (1); the mounting frame (1) being provided with a connection control component (7) for controlling whether the connection member (6) is connected with the mounting frame (1), wherein the connection control component (7) comprises an operation portion (71), a reset portion (72), and a sliding portion (74), all of which are disposed on the mounting frame (1); one end of the sliding portion (74) is connected with the operation portion (71), and the other end is connected with the connection member (6); the sliding portion (74) is capable of being connected with or disengaged from the connection member (6) under the driving of the operation portion (71); the reset portion (72) causes the sliding portion (74) to always have a tendency of moving towards a position where the sliding portion (74) is connected with the connection member (6), wherein the mounting frame (1) comprises an inner casing (15) and an outer casing (13) which are mutually interlocked to form a receiving cavity, and the outer casing (13) is provided with a mounting groove (132) protruding in a direction away from the inner casing (15), and the operation portion (71) is inserted into the mounting groove (132) and movable relative to the mounting groove (132) to be close to or away from a groove bottom (1321) of the mounting groove (132); the reset portion (72) is disposed between the groove bottom (1321) of the mounting groove (132) and the operation portion (71), and the sliding portion (74) is disposed in the receiving cavity.

2. The eye tracking apparatus according to claim 1, wherein the mounting frame (1) comprises a first frame (11) and a second frame (12) that are connected to each other, and the first frame (11) and the second frame (12) are respectively opposite to one eye of the user.

3. The eye tracking apparatus according to claim 2, wherein the hood (3) comprises a first hood (31) and a second hood (32), and the first hood (31) is disposed on the first frame (11) and is capable of providing an enclosure between the first frame (11) and the face of the user; the second hood (32) is disposed on the second frame (12) and capable of providing an enclosure between the second frame (12) and the face of the user.

4. The eye tracking apparatus according to claim 3, wherein at least one of the first hood (31) and the second hood (32) comprises a connection frame (311) and a hood body (312) disposed on the connection frame (311), and the connection frame (311) is connected with the mounting frame (1).

5. The eye tracking apparatus according to claim 4, wherein one of the connection frame (311) and the mounting frame (1) is provided with a plug pin (4), and the other is provided with a plug hole, the plug pin (4) is pluggable into the plug hole.

6. The eye tracking apparatus according to claim 4, wherein the hood body (312) comprises a first portion (3121) and a second portion (3122), which are distributed along a circumferential direction of the connection frame (311), and the first portion (3121) is overlapped with the second portion (3122); a size of an overlapped area of the first portion (3121) and the second portion (3122) is adjustable.

7. The eye tracking apparatus according to claim 4, wherein the hood body (312) is a hood body capable of generating a reversible deformation when being subjected to a force.

8. The eye tracking apparatus according to claim 4, further comprising at least one lens (5) for blocking interferential light, the lens (5) being disposed in the mounting frame (1) or the connection frame (311).

9. The eye tracking apparatus according to claim 1, wherein the connection member (6) is located at a side of the mounting frame (1) away from the hood (3), and comprises a substrate (61), a first connection portion (62) disposed at one end of the substrate (61), and a second connection portion (63) disposed on a side of the substrate (61) away from the first connection portion (62), the first connection portion (62) is configured to be connected with the head-mounted apparatus, and the second connection portion (63) is configured to pass through the outer casing (13) to be connected with the sliding portion (74).

10. The eye tracking apparatus according to claim 9, wherein a positioning protrusion is disposed at a side of the substrate (61) towards the outer casing (13), and a positioning groove corresponding to the positioning protrusion is disposed on the outer casing (13); or the positioning groove is disposed at the side of the substrate (61) towards the outer casing (13), and the positioning protrusion corresponding to the positioning groove is disposed on the outer casing (13).

11. The eye tracking apparatus according to claim 9, wherein the sliding portion (74) comprises a sliding plate (73), and the sliding plate (73) is provided with a third connection portion (731) corresponding to the second connection portion (63), and when the connection control component (7) is in a first state, the third connection portion (731) is cooperated with the outer casing (13) to snap with the connection member (6) so as to fix the connection member (6); when the connection control component (7) is in a second state, a position of the third connection portion (731) relative to the outer casing (13) is changed, and the fixing of the connection member (6) is released.

12. The eye tracking apparatus according to claim 11, wherein the second connection portion (63) comprises a hook, and the third connection portion (731) comprises a long hole, and the hook can pass through the outer casing (13) and move along an extending direction of the long hole.

13. The eye tracking apparatus according to claim 11, wherein the sliding plate (73) is provided with a guiding groove (732), and a guiding block (131) matching with the guiding groove (732) is disposed on a side of the outer casing (13) towards the inner casing (15).

14. The eye tracking apparatus according to claim 13, wherein a limiting platen (8) is disposed on a side of the guide block (131) away from the outer casing (13), and the sliding plate (73) is located between the limiting platen (8) and the outer casing (13), and is capable of abutting against the limiting platen (8) and moving relative to the limiting platen (8).

15. The eye tracking apparatus according to claim 1, wherein the eye tracking component (2) comprises at least one light source (21) and at least one image acquisition component (22), and the light source (21) and the image acquisition component (22) are disposed on the mounting frame (1).

16. The eye tracking apparatus according to claim 15, further comprising a scene camera (100) for acquiring a scene image, and the scene camera (100) is disposed on the mounting frame (1) and configured to be cooperated with the image acquisition component (22) to determine a gaze position of eyes of the user in an usage scene.

17. An eye tracking device comprising a head-mounted apparatus and the eye tracking apparatus according to claim 1.

* * * * *